US012491023B2

(12) United States Patent
Netzel

(10) Patent No.: US 12,491,023 B2
(45) Date of Patent: Dec. 9, 2025

(54) FINE DISSECTION END EFFECTOR ASSEMBLY

(71) Applicant: Covidien LP, Mansfield, MA (US)

(72) Inventor: Kenneth E. Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 845 days.

(21) Appl. No.: 17/061,846

(22) Filed: Oct. 2, 2020

(65) Prior Publication Data

US 2022/0104868 A1 Apr. 7, 2022

(51) Int. Cl.

| | |
|---|---|
| ***A61B 18/14*** | (2006.01) |
| ***A61B 17/29*** | (2006.01) |
| ***A61B 18/00*** | (2006.01) |

(52) U.S. Cl.

CPC .. *A61B 18/1447* (2013.01); *A61B 2017/2947* (2013.01); *A61B 2018/00077* (2013.01); *A61B 2018/00589* (2013.01); *A61B 2018/00595* (2013.01); *A61B 2018/0063* (2013.01); *A61B 2018/1455* (2013.01)

(58) Field of Classification Search

CPC ........ A61B 18/1447; A61B 2017/2947; A61B 2018/00077

See application file for complete search history.

(56) References Cited

U.S. PATENT DOCUMENTS

| | | | |
|---|---|---|---|
| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| 5,170,800 | A | 12/1992 | Smith et al. |
| D343,453 | S | 1/1994 | Noda |
| 5,322,055 | A | 6/1994 | Davison et al. |
| D348,930 | S | 7/1994 | Olson |
| D349,341 | S | 8/1994 | Lichtman et al. |
| D354,564 | S | 1/1995 | Medema |
| D358,887 | S | 5/1995 | Feinberg |
| 5,637,110 | A | 6/1997 | Pennybacker et al. |
| 5,653,721 | A | 8/1997 | Knodel et al. |
| D384,413 | S | 9/1997 | Zlock et al. |
| 5,695,521 | A | 12/1997 | Anderhub |
| 5,776,155 | A | 7/1998 | Beaupre et al. |

(Continued)

OTHER PUBLICATIONS

Extended Search Report for application No. 21200450.1 dated Mar. 1, 2022.

*Primary Examiner* — Joseph A Stoklosa
*Assistant Examiner* — Annie L Shoulders

(57) ABSTRACT

An electrosurgical instrument includes a housing having a handle and an elongated shaft extending therefrom supporting an end effector assembly. The end effector assembly includes first and second jaw members each having a jaw housing and an electrically conductive tissue engaging surface. The first jaw member includes a U-shaped proximal flange that defines a cuff having sides configured to support a pivot and also that define cradles for securing a pivot bar. The second jaw member defines a U-shaped cuff for receiving the proximal flange the first jaw member. The cuff includes sides that define cradles for supporting the pivot thereon through the range of motion between first and second jaw members.

16 Claims, 4 Drawing Sheets

(56) References Cited

U.S. PATENT DOCUMENTS

| | | | |
|---|---|---|---|
| H1745 | H | 8/1998 | Paraschac |
| D402,028 | S | 12/1998 | Grimm et al. |
| D408,018 | S | 4/1999 | McNaughton |
| 5,897,523 | A | 4/1999 | Wright et al. |
| 5,906,628 | A | 5/1999 | Miyawaki et al. |
| 5,944,737 | A | 8/1999 | Tsonton et al. |
| 5,947,984 | A | 9/1999 | Whipple |
| D416,089 | S | 11/1999 | Barton et al. |
| 6,024,750 | A | 2/2000 | Mastri et al. |
| D424,694 | S | 5/2000 | Tetzlaff et al. |
| D425,201 | S | 5/2000 | Tetzlaff et al. |
| H1904 | H | 10/2000 | Yates et al. |
| 6,168,605 | B1 | 1/2001 | Measamer et al. |
| 6,214,023 | B1 | 4/2001 | Whipple et al. |
| D449,886 | S | 10/2001 | Tetzlaff et al. |
| D453,923 | S | 2/2002 | Olson |
| D454,951 | S | 3/2002 | Bon |
| D457,958 | S | 5/2002 | Dycus et al. |
| D457,959 | S | 5/2002 | Tetzlaff et al. |
| H2037 | H | 7/2002 | Yates et al. |
| D465,281 | S | 11/2002 | Lang |
| D466,209 | S | 11/2002 | Bon |
| 6,589,200 | B1 | 7/2003 | Schwemberger et al. |
| D493,888 | S | 8/2004 | Reschke |
| D496,997 | S | 10/2004 | Dycus et al. |
| D499,181 | S | 11/2004 | Dycus et al. |
| D502,994 | S | 3/2005 | Blake, III |
| D509,297 | S | 9/2005 | Wells |
| D525,361 | S | 7/2006 | Hushka |
| 7,083,618 | B2 | 8/2006 | Couture et al. |
| 7,101,371 | B2 | 9/2006 | Dycus et al. |
| D531,311 | S | 10/2006 | Guerra et al. |
| D533,274 | S | 12/2006 | Visconti et al. |
| D533,942 | S | 12/2006 | Kerr et al. |
| D535,027 | S | 1/2007 | James et al. |
| D538,932 | S | 3/2007 | Malik |
| D541,418 | S | 4/2007 | Schechter et al. |
| D541,611 | S | 5/2007 | Aglassinge |
| D541,938 | S | 5/2007 | Kerr et al. |
| D545,432 | S | 6/2007 | Watanabe |
| D547,154 | S | 7/2007 | Lee |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| D582,038 | S | 12/2008 | Swoyer et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| D621,503 | S | 8/2010 | Otten et al. |
| 7,776,065 | B2 * | 8/2010 | Griffiths ................. A61B 17/29 606/207 |
| 7,799,045 | B2 | 9/2010 | Masuda |
| D627,462 | S | 11/2010 | Kingsley |
| D628,289 | S | 11/2010 | Romero |
| D628,290 | S | 11/2010 | Romero |
| 7,846,155 | B2 | 12/2010 | Houser et al. |
| D630,324 | S | 1/2011 | Reschke |
| D649,249 | S | 11/2011 | Guerra |
| D649,643 | S | 11/2011 | Allen, IV et al. |
| D661,394 | S | 6/2012 | Romero et al. |
| D670,808 | S | 11/2012 | Moua et al. |
| D680,220 | S | 4/2013 | Rachlin |
| 8,419,757 | B2 | 4/2013 | Smith et al. |
| 8,444,664 | B2 | 5/2013 | Balanev et al. |
| 8,708,210 | B2 | 4/2014 | Zemlok et al. |
| 8,773,001 | B2 | 7/2014 | Wiener et al. |
| 10,792,064 | B2 | 10/2020 | Craig et al. |
| 2008/0015566 | A1 | 1/2008 | Livneh |
| 2010/0063526 | A1 | 3/2010 | Beaupre et al. |
| 2011/0144678 | A1 * | 6/2011 | Slater ................. A61B 17/3201 606/170 |
| 2012/0116262 | A1 | 5/2012 | Houser et al. |
| 2012/0116264 | A1 | 5/2012 | Haberstich et al. |
| 2012/0116388 | A1 | 5/2012 | Houser et al. |
| 2012/0116394 | A1 | 5/2012 | Timm et al. |
| 2012/0116396 | A1 | 5/2012 | Price et al. |
| 2012/0116433 | A1 | 5/2012 | Houser et al. |
| 2012/0215234 | A1 * | 8/2012 | Chowaniec ........ A61B 17/0469 606/144 |
| 2013/0261642 | A1 * | 10/2013 | Willett ................... A61B 90/03 606/143 |
| 2014/0025070 | A1 | 1/2014 | Kerr et al. |
| 2014/0135804 | A1 | 5/2014 | Weisenburgh, II et al. |
| 2014/0188101 | A1 | 7/2014 | Bales, Jr. et al. |
| 2014/0257284 | A1 * | 9/2014 | Artale ................ A61B 18/1445 606/49 |
| 2014/0284313 | A1 | 9/2014 | Allen, IV et al. |
| 2015/0148831 | A1 | 5/2015 | Faller et al. |
| 2015/0209060 | A1 | 7/2015 | Dmuschewsky |
| 2015/0245866 | A1 | 9/2015 | Twomey et al. |
| 2016/0030072 | A1 * | 2/2016 | Devlin ................... A61B 17/29 606/174 |
| 2016/0345994 | A1 | 12/2016 | Allen, IV |
| 2017/0296199 | A1 | 10/2017 | Beger |
| 2018/0042637 | A1 | 2/2018 | Craig et al. |
| 2020/0305956 | A1 * | 10/2020 | Behymer ........... A61B 17/2833 |
| 2020/0330148 | A1 * | 10/2020 | Weiler ............... A61B 18/1442 |

* cited by examiner

FINE DISSECTION END EFFECTOR ASSEMBLY

FIELD

The present disclosure relates to surgical instruments and, more particularly, to electrosurgical instruments for treating and dissecting tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, dissect or seal, tissue. Typically, prior to tissue being treated, a surgeon must dissect portions of the tissue to orient the tissue for treatment. Examples of dissection include "blunt" dissection wherein the end of the end effector is used to bluntly separate tissue. Other examples include "poke and spread" dissection wherein the tissue is engaged and then the jaw members of the end effector are opened to spread the tissue. Still in other instances, a surgeon may have to finely dissect tissue in a grasp and pull manner.

Once the tissue is treated, the surgeon may have to accurately sever the treated tissue or further dissect portions thereof. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is an electrosurgical instrument that includes a housing having a handle and an elongated shaft extending therefrom supporting an end effector assembly at a distal end thereof. The end effector assembly includes a first jaw member having a jaw housing supporting an electrically conductive tissue engaging surface thereon. The jaw housing has a U-shaped proximal flange including opposing sides defining a cuff therebetween. Each side has a cradle defined therein configured to secure a pivot bar therein. The proximal flange of the first jaw member is configured to operably support a pivot therein.

The end effector assembly also includes a second jaw member having a jaw housing supporting an electrically conductive tissue engaging surface thereon in opposition to the tissue engaging surface of the first jaw member. The jaw housing includes a U-shaped proximal flange having opposing sides defining a cuff therebetween configured to receive the proximal flange of the first jaw member. Each side of the second proximal flange includes a cradle defined therein configured to operably support the pivot and the proximal flange is configured to operably engage the distal end of the elongated shaft.

A drive tube is selectively translatable within the elongated shaft and includes a drive member disposed at a distal end thereof operably secured to the pivot bar. Actuation of the handle translates the drive member which, in turn, translates the pivot bar to rotate the first jaw member relative to the second jaw member about the pivot.

In aspects according to the present disclosure, the pivot bar is welded to the cradle of each side of the proximal flange of the first jaw member. In other aspects according to the present disclosure, the first jaw member moves relative the second jaw member upon actuation of the drive member.

In aspects according to the present disclosure, the second jaw member defines a longitudinal axis therethrough and the pivot is disposed on one side of the longitudinal axis and the pivot bar is offset from the pivot on the other side of the longitudinal axis. In other aspects according to the present disclosure, the cradle of the second jaw member is defined in an upper edge of the proximal flange thereof maximizing the offset between the pivot and the pivot bar increasing mechanical advantage therebetween. In yet other aspects according to the present disclosure, the offset between the pivot and the pivot bar provides a substantially constant closure force between the first and second jaw members through the range of motion therebetween. In still other aspects according to the present disclosure, the offset between the pivot and the pivot bar provides a substantially constant opening and closing force between the first and second jaw members through the range of motion therebetween.

In aspects according to the present disclosure, the elongated shaft defines an outer periphery and wherein the proximal flanges of the first and second jaw members remain inside the outer periphery during the range of motion between jaw members.

Provided in accordance with aspects of the present disclosure is an end effector assembly for an electrosurgical instrument that includes a first jaw member having a jaw housing supporting an electrically conductive tissue engaging surface thereon. The jaw housing includes a U-shaped proximal flange having opposing sides defining a cuff therebetween. Each side includes a cradle defined therein configured to secure a pivot bar therein and the proximal flange is configured to operably support a pivot therein.

The end effector assembly includes a second jaw member having a jaw housing supporting an electrically conductive tissue engaging surface thereon in opposition to the tissue engaging surface of the first jaw member. The jaw housing includes a U-shaped proximal flange having opposing sides defining a cuff therebetween configured to receive the proximal flange of the first jaw member. Each side of the second proximal flange includes a cradle defined therein configured to operably support the pivot. A drive member is operably secured to the pivot bar such that actuation the drive member translates the pivot bar to rotate the first jaw member relative to the second jaw member about the pivot.

In aspects according to the present disclosure, the pivot bar is welded to the cradle of each side of the proximal flange of the first jaw member. In other aspects according to the present disclosure, the first jaw member moves relative the second jaw member upon actuation of the drive member.

In aspects according to the present disclosure, the second jaw member defines a longitudinal axis therethrough and the pivot is disposed on one side of the longitudinal axis and the pivot bar is offset from the pivot on the other side of the longitudinal axis. In other aspects according to the present disclosure, the cradle of the second jaw member is defined in an upper edge of the proximal flange thereof maximizing the offset between the pivot and the pivot bar increasing mechanical advantage therebetween. In still other aspects according to the present disclosure, the offset between the pivot and the pivot bar provides a substantially constant closure force between the first and second jaw members through the range of motion therebetween. In yet other aspects according to the present disclosure, the offset between the pivot and the pivot bar provides a substantially constant opening and closing force between the first and second jaw members through the range of motion therebetween.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
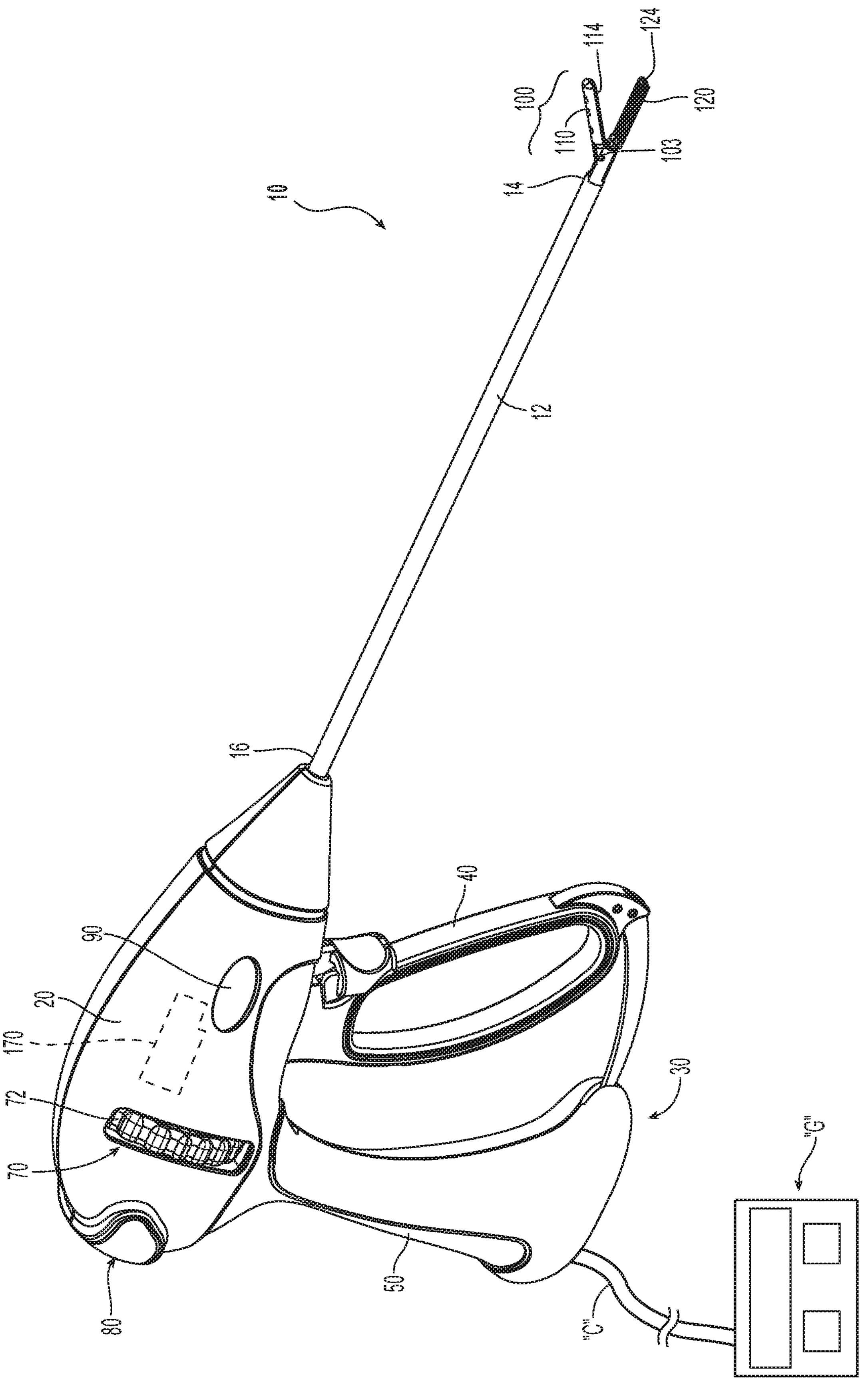
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 (see FIGS. 3A and 3B) to provide energy thereto. First activation switch 80 is coupled to tissue-treating surfaces 114, 124 (FIGS. 1, 3A and 3B) and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element (not shown) of jaw member 120 and the electrosurgical generator "G" for enabling the selective activation of the supply of energy to thermal cutting element 150 for thermally cutting tissue. Details relating to various envisioned thermal cutting elements are disclosed in commonly-owned U.S. Patent Application Ser. No. 63/073,397 [203-13438A], the entire contents of which being incorporated by reference herein.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly 170 (shown generally in phantom) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 3A:
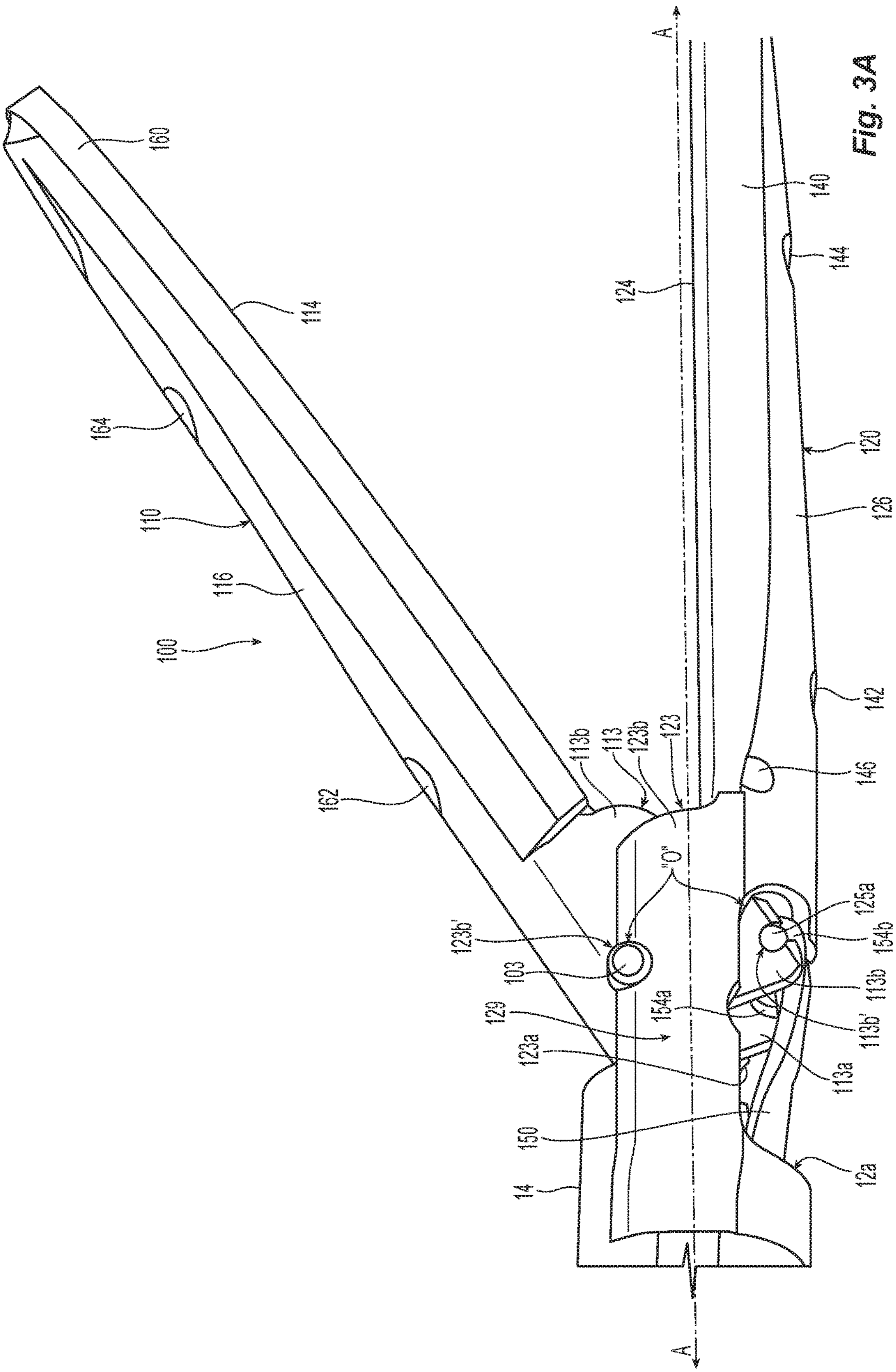
FIG. 3A is a side, perspective view of an end effector assembly having first and second jaw members disposed in a spaced-apart position.
Figure 3B:
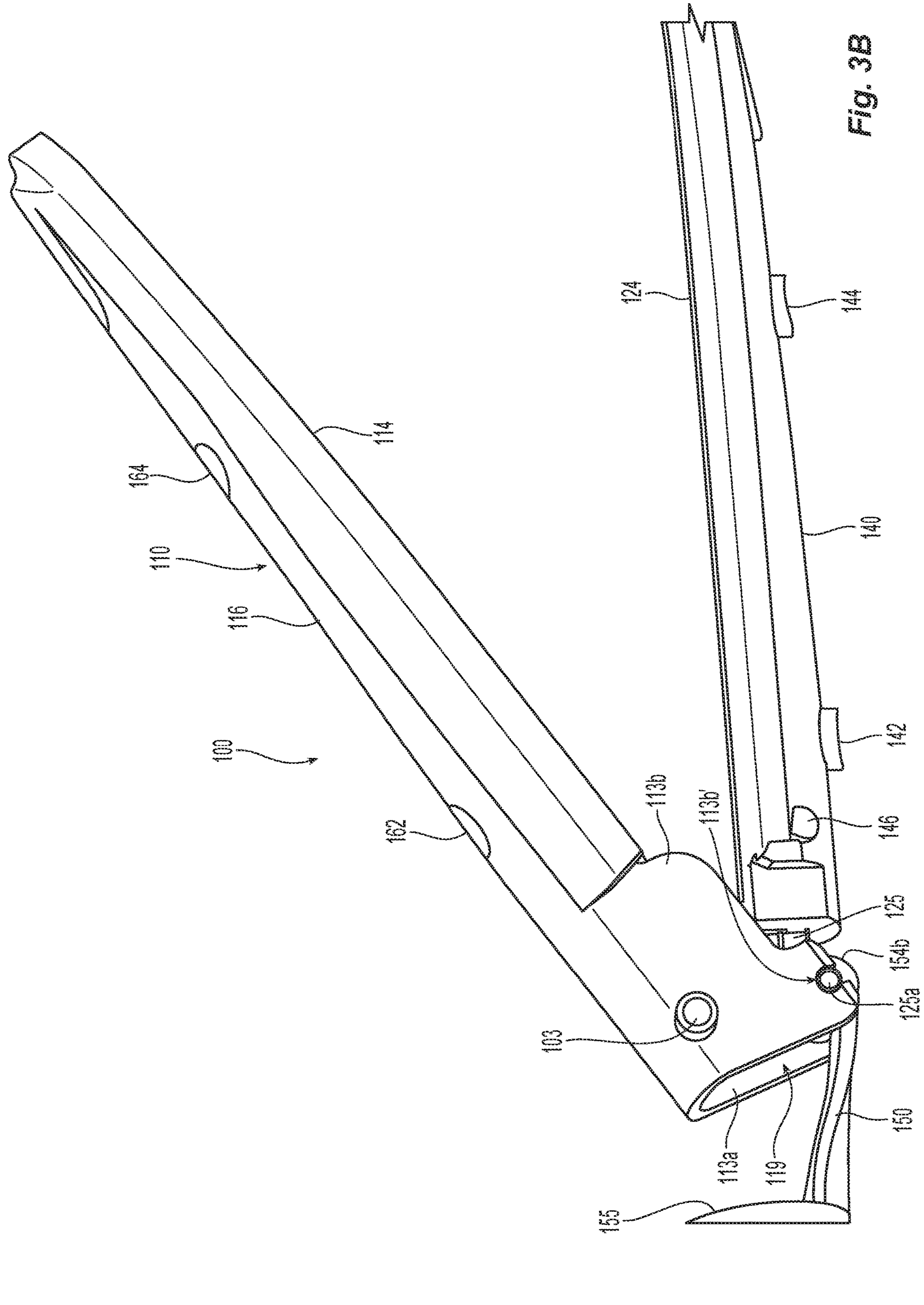
FIG. 3B is a side, perspective view of the end effector assembly of FIG. 3A shown with a housing of the second jaw member removed.

Various drive assemblies 170 are envisioned such as those described in U.S. Pat. Nos. 10,953,757 and 9,113,903, the entire contents of each of which being incorporated by reference herein. The various envisioned drive assemblies 170 are configured to translate a drive member 150 relative to the distal end 14 of the shaft 12 to actuate the jaw members 110, 120 between open and closed positions (FIGS. 3A and 3B). Unilateral and bilateral jaw members 110, 120 are contemplated.

Figure 2:
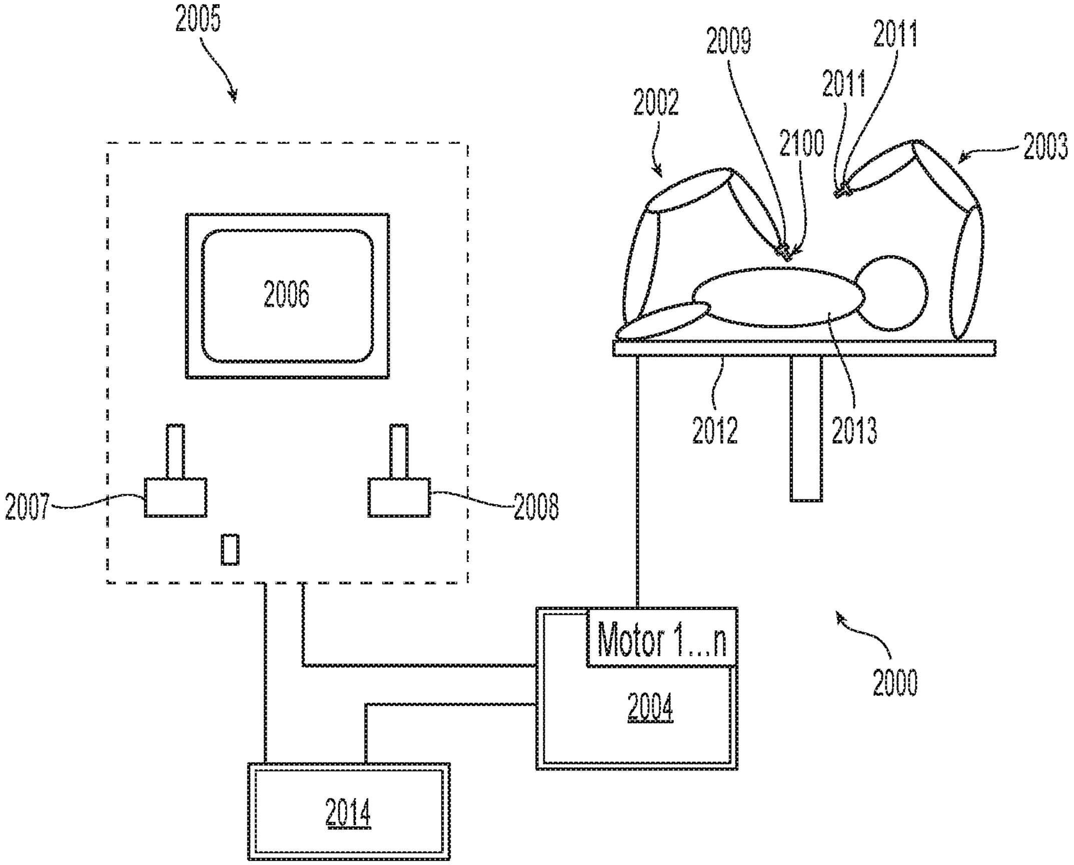
FIG. 2 is a schematic illustration of a robotic surgical instrument provided in accordance with the present disclosure.

Referring to FIG. 2, a robotic surgical instrument provided in accordance with the present disclosure is shown generally identified by reference numeral 2000. Aspects and features of robotic surgical instrument 2000 not germane to the understanding of the present disclosure are omitted to avoid obscuring the aspects and features of the present disclosure in unnecessary detail.

Robotic surgical instrument 2000 includes a plurality of robot arms 2002, 2003; a control device 2004; and an operating console 2005 coupled with control device 2004. Operating console 2005 may include a display device 2006, which may be set up in particular to display three-dimensional images; and manual input devices 2007, 2008, by means of which a surgeon may be able to telemanipulate robot arms 2002, 2003 in a first operating mode. Robotic surgical instrument 2000 may be configured for use on a patient 2013 lying on a patient table 2012 to be treated in a minimally invasive manner. Robotic surgical instrument 2000 may further include a database 21014, in particular coupled to control device 2004, in which are stored, for example, pre-operative data from patient 2013 and/or anatomical atlases.

Each of the robot arms 2002, 2003 may include a plurality of members, which are connected through joints, and an attaching device 2009, 2011, to which may be attached, for example, an end effector assembly 2100, 2200, respectively. End effector assembly 2100 is similar to end effector assembly 100 (FIGS. 3A and 3B), although other suitable end effector assemblies for coupling to attaching device 2009 are also contemplated. End effector assembly 2200 may be any end effector assembly, e.g., an endoscopic camera, other surgical tool, etc. Robot arms 2002, 2003 and end effector assemblies 2100, 2200 may be driven by electric drives, e.g., motors, that are connected to control device 2004. Control device 2004 (e.g., a computer) may be configured to activate the motors, in particular by means of a computer program, in such a way that robot arms 2002, 2003, their attaching devices 2009, 2011, and end effector assemblies 2100, 2200 execute a desired movement and/or function according to a corresponding input from manual input devices 2007, 2008, respectively. Control device 2004 may also be configured in such a way that it regulates the movement of robot arms 2002, 2003 and/or of the motors.

Turning to FIGS. 3A and 3B, one embodiment of a known end effector assembly 100, as noted above, includes first and second jaw members 110, 120. Each jaw member 110, 120 may include a structural support 160, 140, a jaw housing 116, 126, and a tissue-treating surface 114, 124, respectively. Alternatively, only one of the jaw members, e.g., jaw member 120, may include the structural support 140, jaw housing 126, and tissue-treating surface 124. In such embodiments, the other jaw member, e.g., jaw member 110, may be formed as a single unitary body, e.g., a piece of conductive material acting as the structural support 160 and jaw housing 116 and defining the tissue-treating surface 114. An outer surface of the jaw housing 116, in such embodiments, may be at least partially coated with an insulative material or may remain exposed. Tissue-treating surfaces 114, 124 may be pre-formed and engaged with jaw housings 116, 126 via overmolding, adhesion, mechanical engagement, etc. The structural supports 160, 140 for the jaw members 110, 120 may also be engaged to the respective jaw housings 116, 126 in a similar fashion via overmolding, adhesion, mechanical engagement, etc. as explained in more detail below.

As shown in FIGS. 3A and 3B, jaw members 110 and 120 are pivotably supported for rotation about pivot 103 and may be unilateral or bilateral depending upon a particular purpose. Outer housing 116 of jaw member 110 is configured to mechanically engage structural support 160 via one or more detents 162, 164 in a snap-fit manner or during an overmolding step. Jaw member 110 also includes a U-shaped proximal flange 113 having sides 113*a* and 113*b* that cooperatively define a cuff 119 configured to receive the drive member 150 as explained below. The sides 113*a*, 113*b* of flange 113 define opposing pivot bar cradles 113*b*' (other cradle defined in side 113*a* not shown) therein configured to receive a pivot bar 125*a* operably associated therewith.

Pivot bar 125*a* forms part of (or is welded, crimped or riveted or otherwise secured to) the respective cradles 113*b*' of sides 113*a*, 113*b* of the proximal flange 113 during a manufacturing step. The distal end of the drive member 150 is secured (or otherwise engaged) the pivot bar 125*a* while the opposite end of the drive member 150 is secured to or operably associated with the drive tube 155 slidably disposed within a bore 12*a* defined through shaft 12. Upon actuation of the handle 40, drive assembly 170 translate the drive tube 155. The distal end of the drive member 150 may be rotatably secured to the pivot bar 125*a* in a snap-fit or other manner to facilitate smooth operation of the mechanical coupling.

Jaw member 120 includes outer housing 126 configured to mechanically engage structural support 140 via one or more detents 142, 144 in a snap-fit manner or during an overmolding step. Jaw member 120 also includes a U-shaped proximal flange 123 having sides 123*a* and 123*b* that cooperatively define a cuff 129 configured to receive the proximal flange 113 of jaw member 110 as explained below. Flanges 123 and 113 may additionally act as tissue stops. The sides 123*a*, 123*b* of flange 123 define opposing pivot cradles 123*b*' (other cradle defined in side 123*a* not shown) therein configured to receive the pivot 103 operably associated with jaw member 110 (FIG. 3A). Pivot 103 is disposed through sides 113*a*, 113*b* of flange 113 towards an upper end thereof and is configured to allow rotation of jaw member 110. The pivot 103 rotates within the cradles 123*b*' defined in sides 123*a*, 123*b* of proximal flange 123 of jaw member 120 upon translation of the drive member 150 and rotation of the jaw member 110.

The second jaw member 120 defines a longitudinal axis A-A therethrough, the pivot 103 being disposed on one side the longitudinal axis A-A and the pivot bar 125*a* on the other to form an offset "O". Cradles 123*b*' (and other cradle defined in side 123*a*—not shown) may be defined in an uppermost edges of the proximal flanges 123*a*, 123*b* to maximize the distance or offset "O" between the pivot 103 and the pivot bar 125*a* to maximize the mechanical advantage therebetween. It is contemplated that the offset "O" between the pivot 103 and the pivot bar 125*a* provides a substantially constant opening and closure force between the first and second jaw members 110, 120 through the range of motion therebetween.

Jaw member 120 is secured to the distal end 14 of shaft 12. By mounting the pivot 103 within cradle 123*b*' (and cradle of side 123*a*) and securing jaw member 120 to the end 14 of the shaft 12, the end effector assembly 100 is held secure relative to the shaft 12. Actuating the handle 40 to translate drive tube 155 and, in turn, drive member 150, will pivot jaw member 110 relative to jaw member 120 by virtue of pivot bar 125*a* camming within the sides 113*a*, 113*b* of the proximal flange 113 about pivot 103.

Securing the pivot bar 125*a* to the sides 113*a*, 113*b* of the proximal flange 113 which, in turn, is directly coupled to the drive tube 155, minimizes hysteresis between the various mechanical components allowing finer dissection capabilities and a more consistent jaw closure and opening force. Providing consistent jaw closure forces and resulting sealing pressures between jaw members 110, 120 produces more consistent sealing and subsequent cutting of tissue and facilitates dissection. Moreover, with near constant closure forces throughout the entire handle 40 stroke, opening and closing the jaw members 110, 120 during poke and spread type dissection, translates to a consistent force therebetween enhancing the overall feel of the instrument during use.

Further, the mechanical couplings, i.e., drive tube 155 to drive member 150 to pivot bar 125*a* to proximal flange 113, do not extend outside the overall dimensions of the outer periphery of the elongated shaft 12 which reduces the chances of catching tissue during use while also maximizing the area for knife translation if used with a mechanical knife (Not shown).

The offset design of the pivot bar 125*a* and the pivot 103 provides a large mechanical advantage when the jaw members 110, 120 are being approximated about tissue but less of a mechanical advantage when the jaw members 110, 120 are moved to a fully open position. However, over the stroke of the closure of the jaw members 110, 120, the offset mechanical arrangement of the pivot bar 125*a* and the pivot 103 will yield more consistent closure pressure against tissues of varying sizes. Moreover, the near constant opening and closure forces provide the user with a consistent feel when opening and closing the jaw members 110, 120 for fine dissection purposes.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a housing including a handle and an elongated shaft extending therefrom supporting and end effector assembly at a distal end thereof, the end effector assembly including:
      a first jaw member having a first jaw housing supporting an electrically conductive tissue engaging surface thereon, the first jaw housing including a first U-shaped proximal flange having opposing sides defining a cuff therebetween, a lower edge of each side including a first cradle defined therein configured to secure a pivot bar therein, the first proximal flange configured to operably support a pivot therein; and
      a second jaw member having a second jaw housing supporting an electrically conductive tissue engaging surface thereon in opposition to the tissue engaging surface of the first jaw member, the second jaw housing including a second U-shaped proximal flange having opposing sides defining a cuff therebetween configured to receive the first proximal flange of the first jaw member, an upper edge of each side of the second proximal flange including a second cradle recessed into the upper edge of each side and configured to receive the pivot, the second proximal flange configured to operably engage the distal end of the elongated shaft; and
   a drive tube selectively translatable within the elongated shaft, the drive tube including a drive member disposed at a distal end thereof operably secured to the pivot bar wherein actuation of the handle translates the drive member which, in turn, moves the pivot bar and the first cradle relative to the pivot to rotate the first jaw member relative to the second jaw member about the pivot supported within the second cradle, the pivot and the pivot bar maintaining a fixed distance relative to one another during translation of the drive member.

2. The electrosurgical instrument according to claim 1, wherein the pivot bar is welded, crimped or riveted to the cradle of each side of the first proximal flange of the first jaw member.

3. The electrosurgical instrument according to claim 1, wherein the first jaw member moves relative the second jaw member upon actuation of the drive member.

4. The electrosurgical instrument according to claim 1, wherein the second jaw member defines a longitudinal axis therethrough, the pivot being disposed on one side of the longitudinal axis and the pivot bar being offset from the pivot on the other side of the longitudinal axis.

5. The electrosurgical instrument according to claim 4, wherein the second cradle of the second jaw member is defined in an upper edge of the second proximal flange maximizing the offset between the pivot and the pivot bar increasing mechanical advantage therebetween.

6. The electrosurgical instrument according to claim 5, wherein the offset between the pivot and the pivot bar provides a substantially constant closure force between the first and second jaw members through the range of motion therebetween.

7. The electrosurgical instrument according to claim 5, wherein the offset between the pivot and the pivot bar provides a substantially constant opening and closing force between the first and second jaw members through the range of motion therebetween.

8. The electrosurgical instrument according to claim 1, wherein the elongated shaft defines an outer periphery and wherein the proximal flanges of the first and second jaw members remain inside the outer periphery during the range of motion between jaw members.

9. An end effector assembly for an electrosurgical instrument, comprising:
   a first jaw member having a first jaw housing supporting an electrically conductive tissue engaging surface thereon, the first jaw housing including a first U-shaped proximal flange having opposing sides defining a cuff therebetween, each side including a first cradle defined therein configured to secure a pivot bar therein, the first proximal flange configured to operably support a pivot therein;
   a second jaw member having a second jaw housing supporting an electrically conductive tissue engaging surface thereon in opposition to the tissue engaging surface of the first jaw member, the second jaw housing including a second U-shaped proximal flange having opposing sides defining a cuff therebetween configured to receive the first proximal flange of the first jaw member, an upper edge of each side of the second proximal flange including a second cradle recessed into the upper edge of each side and configured to receive the pivot; and
   a drive member operably secured to the pivot bar wherein actuation of the drive member moves the pivot bar and the first cradle relative to the pivot to rotate the first jaw member relative to the second jaw member about the pivot supported within the second cradle, the pivot and the pivot bar maintaining a fixed distance relative to one another during actuation of the drive member to translate the pivot bar.

10. The end effector assembly according to claim 9, wherein the pivot bar is welded, crimped or riveted to the cradle of each side of the first proximal flange of the first jaw member.

11. The end effector assembly according to claim 9, wherein the first jaw member moves relative the second jaw member upon actuation of the drive member.

12. The electrosurgical instrument according to claim 9, wherein the second jaw member defines a longitudinal axis therethrough, the pivot being disposed on one side of the longitudinal axis and the pivot bar being offset from the pivot on the other side of the longitudinal axis.

13. The end effector assembly according to claim 12, wherein the cradle of the second jaw member is defined in an upper edge of the second proximal flange thereof maximizing the offset between the pivot and the pivot bar increasing mechanical advantage therebetween.

14. The end effector assembly according to claim 13, wherein the offset between the pivot and the pivot bar provides a substantially constant closure force between the first and second jaw members through the range of motion therebetween.

15. The end effector assembly according to claim 13, wherein the offset between the pivot and the pivot bar provides a substantially constant opening and closing force between the first and second jaw members through the range of motion therebetween.

16. An electrosurgical instrument, comprising:

a housing including a handle and an elongated shaft extending therefrom supporting and end effector assembly at a distal end thereof, the end effector assembly including:

a first jaw member having a first jaw housing supporting an electrically conductive tissue engaging surface thereon, the first jaw housing including a first U-shaped proximal flange having opposing sides defining a cuff therebetween, each side including a first cradle defined therein configured to secure a pivot bar therein, the first proximal flange configured to operably support a pivot therein, wherein the pivot bar is welded, crimped or riveted to the first cradle on each side of the first proximal flange of the first jaw member;

a second jaw member having a second jaw housing supporting an electrically conductive tissue engaging surface thereon in opposition to the tissue engaging surface of the first jaw member, the second jaw housing including a second U-shaped proximal flange having opposing sides defining a cuff therebetween configured to receive the first proximal flange of the first jaw member, an upper edge of each side of the second proximal flange including a second cradle recessed into the upper edge of each side and configured to receive the pivot, the second proximal flange configured to operably engage the distal end of the elongated shaft; and a drive tube selectively translatable within the elongated shaft, the drive tube including a drive member disposed at a distal end thereof operably secured to the pivot bar wherein actuation of the handle translates the drive member which, in turn, moves the pivot bar and the first cradle relative to the pivot to rotate the first jaw member relative to the second jaw member about the pivot supported within the second cradle, and wherein the second jaw member defines a longitudinal axis therethrough, the pivot being disposed on one side of the longitudinal axis and the pivot bar being offset from the pivot on the other side of the longitudinal axis and wherein the position of the second cradle is configured to maximize the offset between the pivot and the pivot bar increasing mechanical advantage therebetween.

* * * * *